United States Patent [19]
Nardella et al.

[11] Patent Number: 5,944,022
[45] Date of Patent: Aug. 31, 1999

[54] CATHETER POSITIONING SYSTEM

[75] Inventors: Paul C. Nardella, Wareham; Thomas A. Wrublewski, Sharon, both of Mass.

[73] Assignee: American Cardiac Ablation Co. Inc., Taunton, Mass.

[21] Appl. No.: 08/847,684

[22] Filed: Apr. 28, 1997

[51] Int. Cl.[6] .................................................. A61B 19/00
[52] U.S. Cl. ........................................................ 128/899
[58] Field of Search ............................ 128/899; 600/547, 600/373, 382

[56] References Cited

U.S. PATENT DOCUMENTS

| | | | |
|---|---|---|---|
| 5,201,900 | 4/1993 | Nardella | 606/157 |
| 5,293,868 | 3/1994 | Nardella | 128/642 |
| 5,295,484 | 3/1994 | Marcus et al. | 128/660.03 |
| 5,341,807 | 8/1994 | Nardella | 128/642 |
| 5,357,956 | 10/1994 | Nardella | 128/642 |
| 5,364,392 | 11/1994 | Warner et al. | 606/34 |
| 5,383,917 | 1/1995 | Desai et al. | 607/702 |
| 5,409,000 | 4/1995 | Imran | 128/642 |
| 5,417,687 | 5/1995 | Nardella et al. | 606/32 |
| 5,425,367 | 6/1995 | Shaprio et al. | 128/899 |
| 5,425,382 | 6/1995 | Golden et al. | 128/899 |
| 5,443,489 | 8/1995 | Ben-Haim | 607/115 |
| 5,447,529 | 9/1995 | Marchlinski et al. | 607/99 |
| 5,514,130 | 5/1996 | Baker | 606/41 |
| 5,536,267 | 7/1996 | Edwards et al. | 606/41 |
| 5,540,655 | 7/1996 | Edwards et al. | 604/22 |
| 5,540,679 | 7/1996 | Fram et al. | 606/27 |
| 5,540,681 | 7/1996 | Strul et al. | 606/34 |
| 5,554,110 | 9/1996 | Edwards et al. | 604/22 |
| 5,558,091 | 9/1996 | Acker et al. | 128/899 |
| 5,573,533 | 11/1996 | Strul | 606/34 |
| 5,578,007 | 11/1996 | Imran | 604/95 |
| 5,697,377 | 12/1997 | Wittkampf | 128/899 |

OTHER PUBLICATIONS

*New Three Dimensional Localization Technique for Endocardial Electrodes*, American Heart Association, Abstracts for the 69th Scientific Sessions, New Orleans Convention Center, New Orleans, Louisiana, Nov. 10–13, 1996, Supplement to Circulation, vol. 94, No. 8, Oct. 15, 1996, three pages.

*Primary Examiner*—John P. Lacyk
*Attorney, Agent, or Firm*—Nutter, McClennen & Fish, LLP

[57] ABSTRACT

A system for detecting the position of a catheter in a patient includes three sets of reference electrodes, with one set disposed on each of the mutually orthogonal X, Y and Z axes. A signal processor measures the differential voltage indicative of impedance between a detection electrode disposed on the catheter and each electrode of each of the three sets of reference electrodes in order to determine the X coordinate, Y coordinate and Z coordinate of the catheter. The detected position of the catheter is recorded and the detection of subsequent catheter positions is performed relative to the recorded catheter position. The difference between subsequent catheter positions and the recorded position relative to the X, Y and Z axes is displayed in order to facilitate re-positioning of the catheter at the recorded position. Optional EKG and/or respiratory sensors may be used to synchronize the catheter position detection in order to reduce detection inaccuracies due to EKG and/or respiratory artifacts.

23 Claims, 10 Drawing Sheets

CATHETER POSITIONING SYSTEM

CROSS REFERENCE TO RELATED APPLICATIONS

Not Applicable.

STATEMENTS REGARDING FEDERALLY SPONSORED RESEARCH

Not Applicable.

BACKGROUND OF THE INVENTION

Catheters of the type which are inserted into a vessel of a patient for carrying electrical signals to and from the patient are used in various applications. For example, cardiac catheters are inserted within a blood vessel into a patient's heart to detect cardiac electrical signals, to apply electrical stimulation for diagnostic testing and to apply treatment signals, such as tissue ablation signals which are used to eliminate the source of an arrhythmia. Other applications for ablation catheters include the treatment of tumors, such as breast or liver tumors, and the identification of tumor biopsy sampling sites. In addition to one or more electrodes, the catheter may include other structures, such as a lumen through which light, thermal energy or chemical agents are delivered and/or a sampling system for sampling a tissue or fluid specimen.

One multi-electrode catheter arrangement, described in U.S. Pat. No. 5,341,807 (Nardella), includes signal processing circuitry for detecting contact of the catheter with tissue, such as a vessel wall. The Nardella catheter includes a tip electrode and a plurality of ring electrodes spaced along the catheter. The differential voltage indicative of impedance between the electrodes is measured to provide an indication of the catheter electrodes being disposed in different mediums (for example, when one electrode is in blood and another is in contact with tissue). The resulting indication of catheter contact is useful in many applications. For example, in cardiac ablation, the catheter must be in contact with, or at least in close proximity to, the treatment site in order to ensure that an effective level of RF energy reaches the tissue.

It is generally necessary to utilize a visualization technique of some sort in order to guide the catheter to a desired site of diagnosis and/or treatment and to ensure that the catheter remains at the desired location. Additionally, it is often desirable or necessary to re-position the catheter at a particular location. For example, in applications in which a cardiac ablation catheter is used for diagnosis and subsequent treatment of an arrhythmia, the catheter is moved around the heart while cardiac electrical signals are monitored, following which one or more sites identified as being the source of an arrhythmia are ablated. Thus, during such a procedure, it is necessary to determine the location of the catheter as the electrical signals are monitored in order to facilitate re-positioning the catheter at the site of an arrhythmia for ablation. Further, during any catheter procedure, the catheter may slip and require re-positioning in order to successfully complete the procedure.

Catheter positioning and re-positioning has conventionally been achieved with the use of fluoroscopic techniques. However, since fluoroscopy typically provides only two-dimensional information, its accuracy in catheter positioning is limited. Furthermore, due to the potential risks associated with exposure to electromagnetic radiation, it is advantageous to limit the use of fluoroscopy.

SUMMARY OF THE INVENTION

The invention relates to a catheter positioning system for detecting the position of a catheter relative to mutually orthogonal X, Y and Z axes and for permitting the catheter to be accurately re-positioned with an accuracy on the order of about one millimeter. Once the catheter is placed at a desired location, its position is recorded. Subsequent positions of the catheter are processed relative to the recorded position and are displayed. The catheter is re-positioned at the recorded position by moving the catheter until the displayed difference between the subsequent and recorded catheter positions decreases to zero. With this arrangement, once a desired location is detected and recorded, the fluoroscopic equipment can be turned off, thereby advantageously limiting the patient's exposure to potentially harmful radiation. Further, the accuracy with which the catheter is re-positioned is enhanced, as compared to the use of fluoroscopic techniques for this purpose.

The position detection system includes a first set of reference electrodes disposed along the X axis, a second set of reference electrodes disposed along the Y axis, and a third set of reference electrodes disposed along the Z axis. A signal processor measures the differential voltage indicative of impedance between a detection electrode on the catheter and each electrode of the first, second and third sets of reference electrodes to determine the X coordinate, Y coordinate and Z coordinate of the catheter position, respectively. To this end, a first current provided by an energy source flows between the first set of reference electrodes, a second current flows between the second set of reference electrodes and a third current flows between the third set of reference electrodes. Preferably, the first, second and third currents have different frequencies in order to minimize any cross-axis interference.

In one embodiment, the signal processor includes an X axis processor unit coupled to the first set of reference electrodes, a Y axis processor unit coupled to the second set of reference electrodes and a Z axis processor unit coupled to the third set of reference electrodes. Each of the processor units includes a differential amplifier having a first input coupled to the detection electrode and a second input coupled to the respective set of reference electrodes. With this particular arrangement, the output of the differential amplifier is substantially null when the impedance between the detection electrode and each electrode of the respective set of reference electrodes is substantially equal. Each of the processor units further includes a demodulator coupled to the output of the differential amplifier for providing a DC signal proportional to the position of the catheter relative to the respective axis (i.e., the coordinate).

An optional EKG sensor detects an EKG signal of the patient for use in synchronizing detection of the catheter position. Further, an optional respiratory sensor detects a respiratory signal of the patient for use in synchronizing detection of the catheter position. In this way, artifacts due to the EKG signal and/or the respiratory signal of the patient are reduced, thereby enhancing the accuracy of the catheter position detection.

The reference electrodes may be needle electrodes inserted into the patient's body in the region of catheter treatment or, alternatively, may be pad electrodes attached externally to the patient's body. In the later case, an additional set of electrodes, referred to as compensation electrodes, is positioned along each of the X, Y and Z axes in order to compensate for any impedance effects due to external attachment of the pad electrodes.

In one embodiment, the detection electrode is positioned at the tip of the catheter and the catheter further includes a proximal electrode and a reference electrode positioned between the tip and the proximal electrode. Contact of the catheter with tissue, such as a vessel wall, is detected by measuring the differential voltage indicative of impedance between the tip electrode and the proximal electrode relative to the reference electrode.

DETAILED DESCRIPTION OF THE INVENTION

Figure 1:
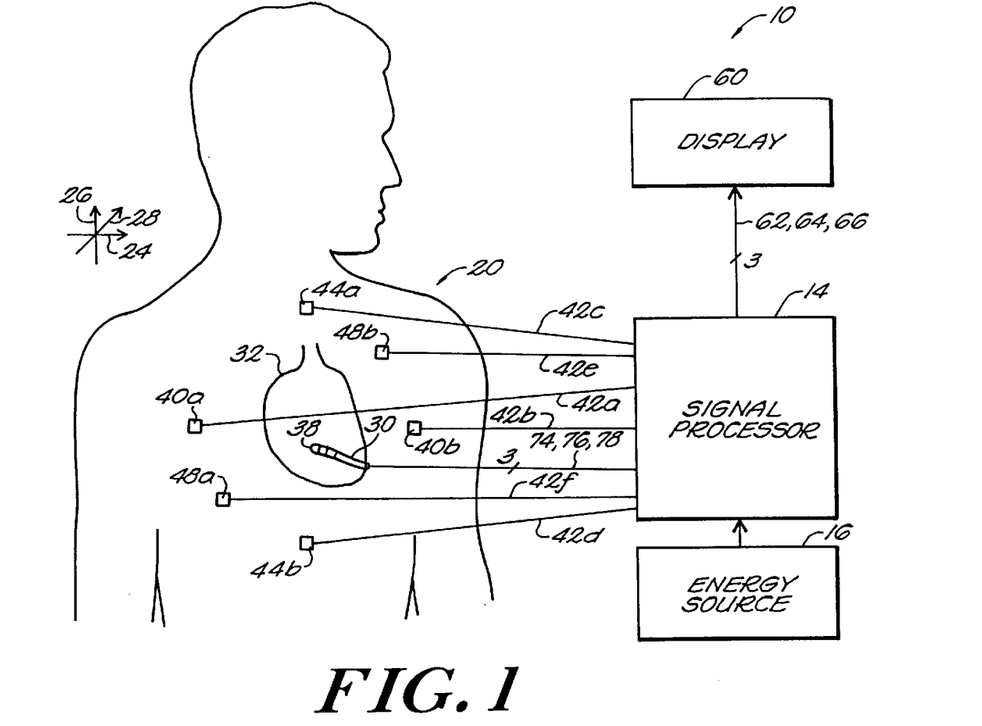
FIG. 1 illustrates a catheter positioning system in accordance with the invention.

Referring to FIG. 1, a catheter positioning system 10 for detecting the position of a catheter 30 having a detection electrode 38 is shown. The system 10 includes a signal processor 14 and three pairs of reference electrodes 20, with one pair positioned along each of three mutually orthogonal axes, including the X axis 24, the Y axis 26 and the Z axis 28. More particularly, a first set of reference electrodes 40a, 40b is positioned along the X axis 24, a second set of reference electrodes 44a, 44b is positioned along the Y axis 26, and a third set of reference electrodes 48a, 48b is positioned along the Z axis 28. An energy source 16 supplies electrical energy to the detection electrode 38 and reference electrodes 20 and a display 60 coupled to the signal processor 14 displays the detected catheter position in a manner that facilitates catheter re-positioning, as will be described. In applications in which the detection electrode 38 delivers ablation energy, the electrode may be referred to as an active electrode.

The illustrated catheter 30 is a cardiac ablation catheter adapted for insertion through a vessel into a patient's heart 32 for arrhythmia diagnosis and ablation. It will be appreciated by those of ordinary skill in the art, however, that the catheter positioning system 10 and related techniques described herein are suitable for use with any catheter application in which it is advantageous to re-position the catheter at a particular location.

The reference electrodes 20 may be needle electrodes adapted for insertion into the patient's body. Alternatively, the reference electrodes 20 may be electrode pads, or patches adapted for external attachment to the patient's skin. Where the electrodes are externally attached, three additional sets of electrodes, referred to as compensation electrodes, are provided to compensate for any impedance effects associated with attachment of the pads to the patient's skin, as will be described further in conjunction with FIG. 9.

Each of the reference electrodes 20 is electrically coupled to the signal processor 14 via a respective signal line 42a–42f, as shown. In the illustrative embodiment, the catheter 30 is coupled to the signal processor 14 via three signal lines 74, 76 and 78, with one signal line coupled to each electrode on the catheter, as described below in conjunction with FIG. 1A.

The energy source 16 delivers AC energy in the form of voltage or current to the electrodes via the signal processor 14 in order to permit voltage measurements to be made by the signal processor. The measured voltage is indicative of impedance since voltage is proportional to impedance. In the illustrative embodiment, the energy source 16 provides a first current to the first set of reference electrodes 40a, 40b, a second current to the second set of reference electrodes 44a, 44b and a third current to the third set of reference electrodes 48a, 48b. Preferably, each of these currents has a different frequency in order to minimize any cross-axis interference. In one example, the first current is a 48 KHz AC current, the second current is a 50 KHz AC current and the third current is a 54 KHz AC current.

Signal processor 14 measures the differential voltage indicative of impedance between the detection electrode 38 of the catheter 30 and each of the six reference electrodes 20 in order to determine the three-dimensional position of the catheter 30 and, specifically, to determine the X coordinate, Y coordinate and Z coordinate of the catheter 30. To this end, the signal processor 14 includes an X axis processor unit 50, a Y axis processor unit 52 and a Z axis processor unit 54 (FIG. 2), with each processor unit measuring the differential voltage indicative of impedance between the detection electrode 38 and each one of the electrodes of the respective set of electrodes. For example, the X axis processor unit 50 measures the voltage indicative of impedance between the detection electrode 38 and reference electrode 40a and also between detection electrode 38 and reference electrode 40b in order to determine the X coordinate of the catheter 30 (i.e., the position of the catheter relative to the X axis).

The signal processor 14 provides an X axis output signal 62, a Y axis output signal 64 and a Z output axis signal 66 coupled to the display 60, which may be referred to alternatively as the catheter location map. The display 60 provides an indication of the position of the catheter relative to the X, Y and Z axes and/or relative to a previously recorded position. More particularly, the catheter positioning system 10 is capable of operating in a "direct" mode of operation, during which the catheter position is continuously tracked and an indication thereof is displayed, or in a "relative" mode of operation, in which a position of the catheter is recorded, subsequent position measurements are made relative to the recorded position and the difference between the recorded and subsequent positions is displayed, as will be described further below.

The display 60 may take various forms, including analog or digital. In one embodiment, two axes are displayed on one graph and the third axis is displayed on a separate device, such as a digital meter. Alternatively, a three axis graphical representation, a wire frame representation, or a surface rendering technique, all of which are conventional Computer-Aided Design (CAD) system presentations, may be used to provide the display 60.

Figure 1A:
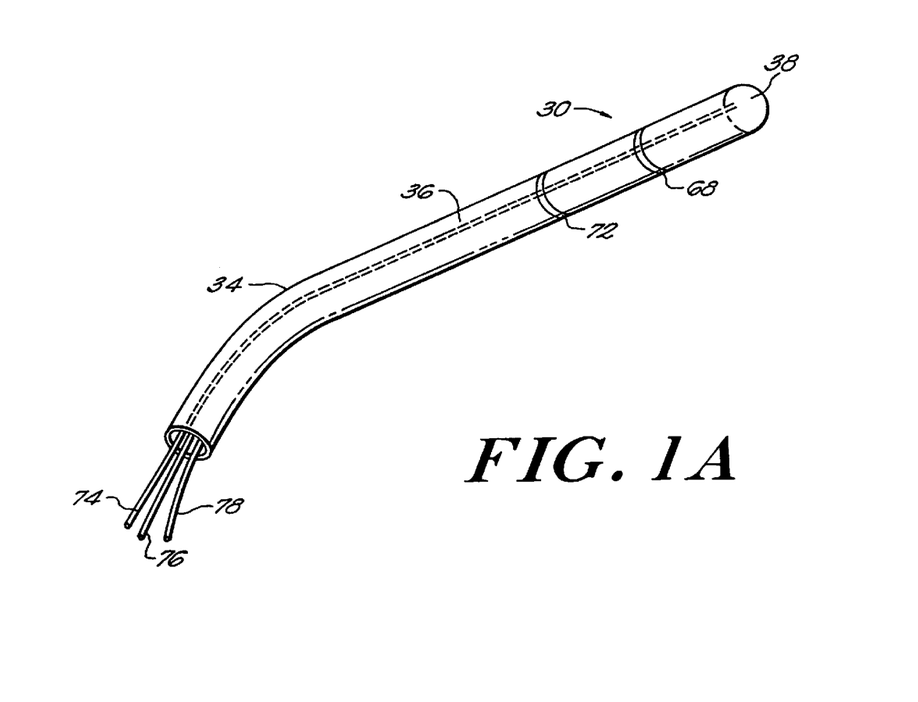
FIG. 1A is a perspective view of a multi-electrode catheter for use with the catheter positioning system of FIG. 1.

Referring also to FIG. 1A, an enlarged view of the illustrative cardiac ablation catheter 30 is shown. The detection electrode 38 which may deliver ablation energy is positioned at the distal tip of the catheter and thus, may be referred to as the tip electrode 38. The catheter 30 further includes a proximal electrode 72 and a reference electrode 68 disposed between the proximal electrode and the tip electrode, with the proximal and reference electrodes being in the form of ring electrodes, as shown. The catheter 30 has an elongated insulating body 36 mounted at the end of a flexible tube 34 which is used for inserting and manipulating the catheter along a vessel. Signal lines 74, 76, and 78 extend from the tube 34 to electrically connect catheter electrodes 38, 68 and 78 to the signal processor 14, respectively. In accordance with a feature of the invention, a fourth current provided by the energy source 16 flows between the tip electrode 38 and proximal electrode 72 in order to facilitate measurements used to determine catheter contact, as described below in conjunction with FIG. 8.

Figure 2:
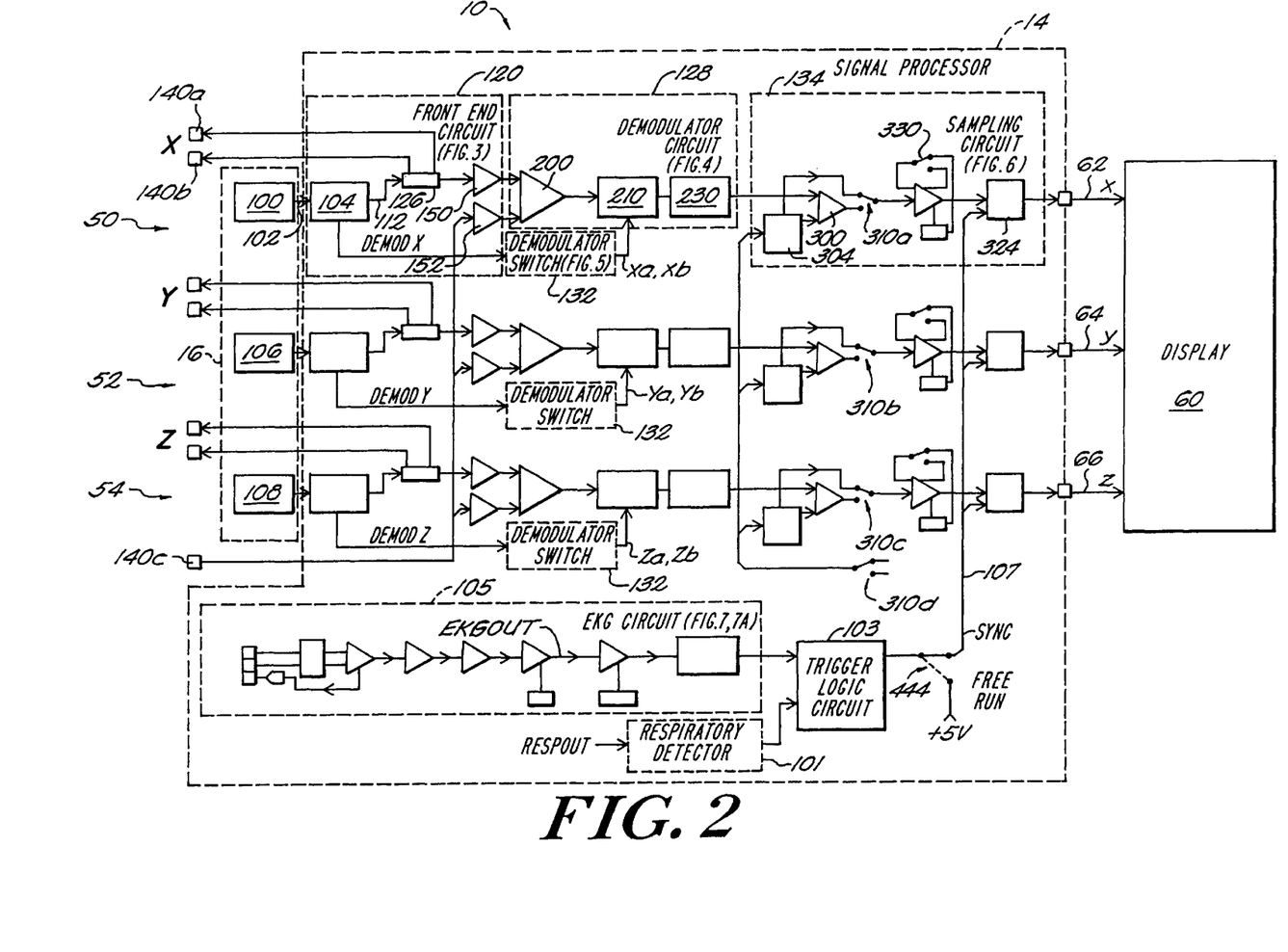
FIG. 2 is block diagram of the catheter positioning system of FIG. 1.

Referring also to FIG. 2, a block diagram of the catheter positioning system 10 is shown to include the signal processor 14, energy source 16 and display 60. The energy source 16 includes three oscillators 100, 106 and 108 for providing the first current to the X axis reference electrodes 40a, 40b, the second current to the Y axis reference electrodes 44a, 44b and the third current to the Z axis reference electrodes 48a, 48b, respectively.

The signal processor 14 includes the X axis processor unit 50 which is coupled to the X axis reference electrodes 40a, 40b, the Y axis processor unit 52 which is coupled to the Y axis reference electrodes 44a, 44b, and the Z axis processor unit 54 which is coupled to the Z axis reference electrodes 48a, 48b, all of which are substantially identical in construction. The processor units will be described with reference to exemplary X axis processor unit 50 for simplicity of discussion. Also provided in the signal processor 14 is an optional EKG circuit 105 (FIGS. 7 and 7A) which monitors the EKG signal of the patient and an optional respiratory detector 101 which monitors the respiratory signal of the patient. The output signals from the EKG circuit 105 and the respiratory detector 101 are processed by a trigger logic circuit 103 to provide a SYNC signal 107 which is used to synchronize catheter position detection, as will be described.

Figure 5:
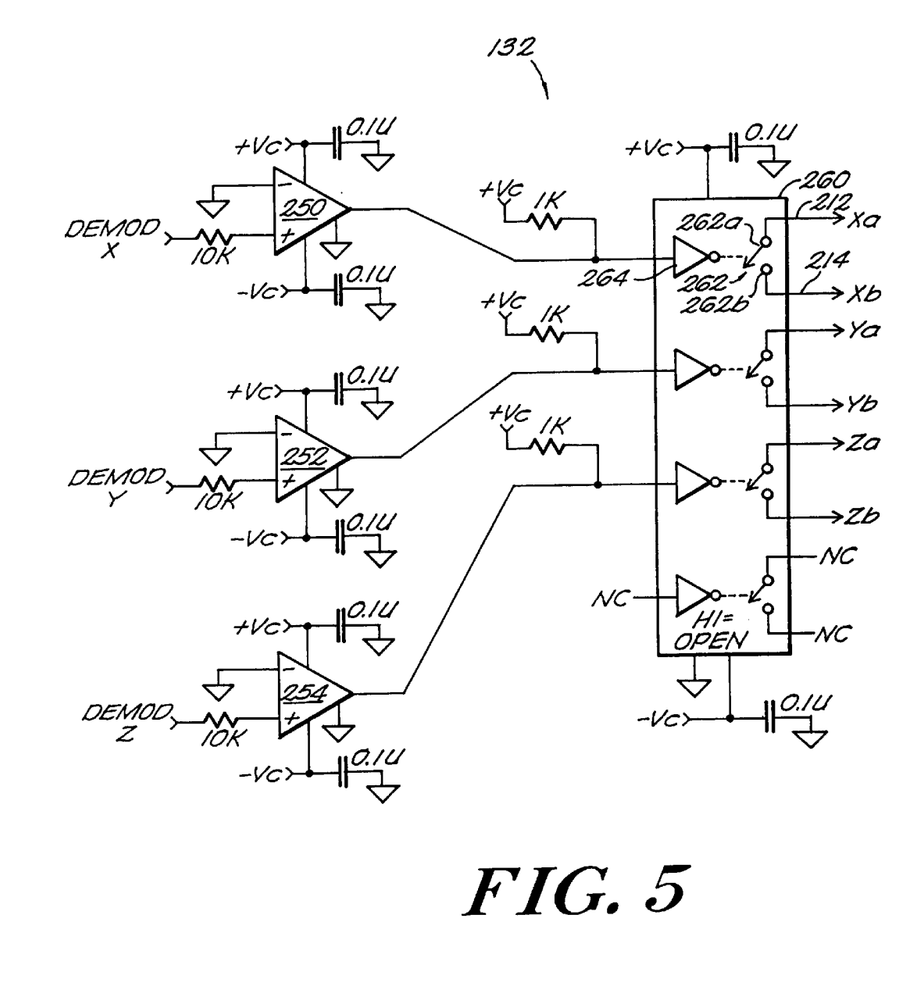
FIG. 5 is a schematic of the demodulator switch of the catheter positioning system of FIG. 2.
Figure 6:
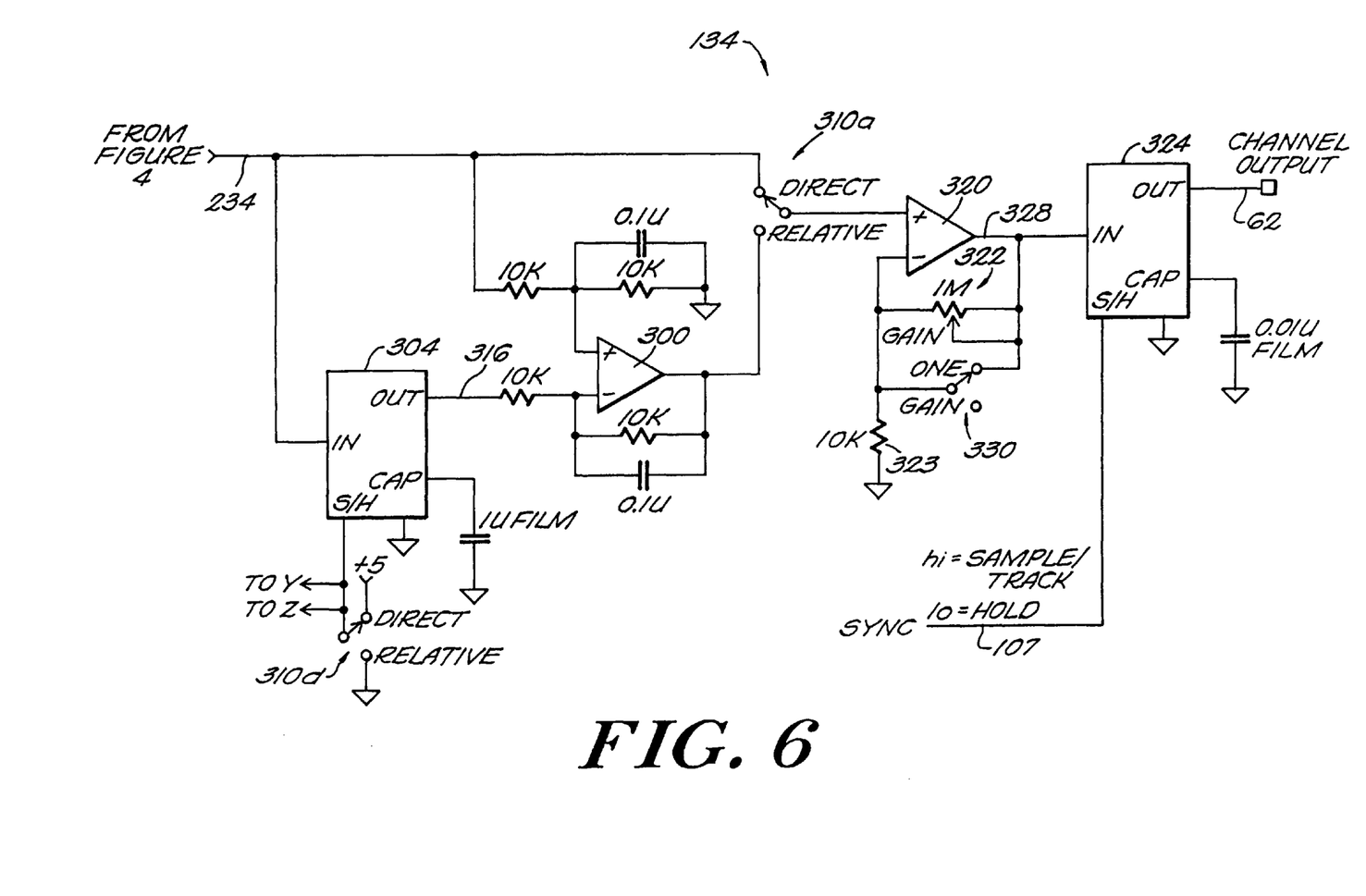
FIG. 6 is a schematic of the sampling circuit of the catheter positioning system FIG. 2.

The processor unit 50 includes a front end circuit 120 (FIG. 3) coupled to the reference electrodes 40a, 40b via respective terminals 140a, 140b of a connector 140, a demodulator circuit 128 (FIG. 4) coupled to the outputs of the front end circuit 120 and a sampling circuit 134 (FIG. 6). The demodulator circuit 128 is responsive to a demodulator switch 132 (FIG. 5). The sampling circuit 134 provides the X axis output signal 62 to the display 60, as shown. It will be appreciated by those of ordinary skill in the art that the particular circuitry arrangement and component values described herein are illustrative only and may be varied without departing from the spirit from the invention.

Figure 3:
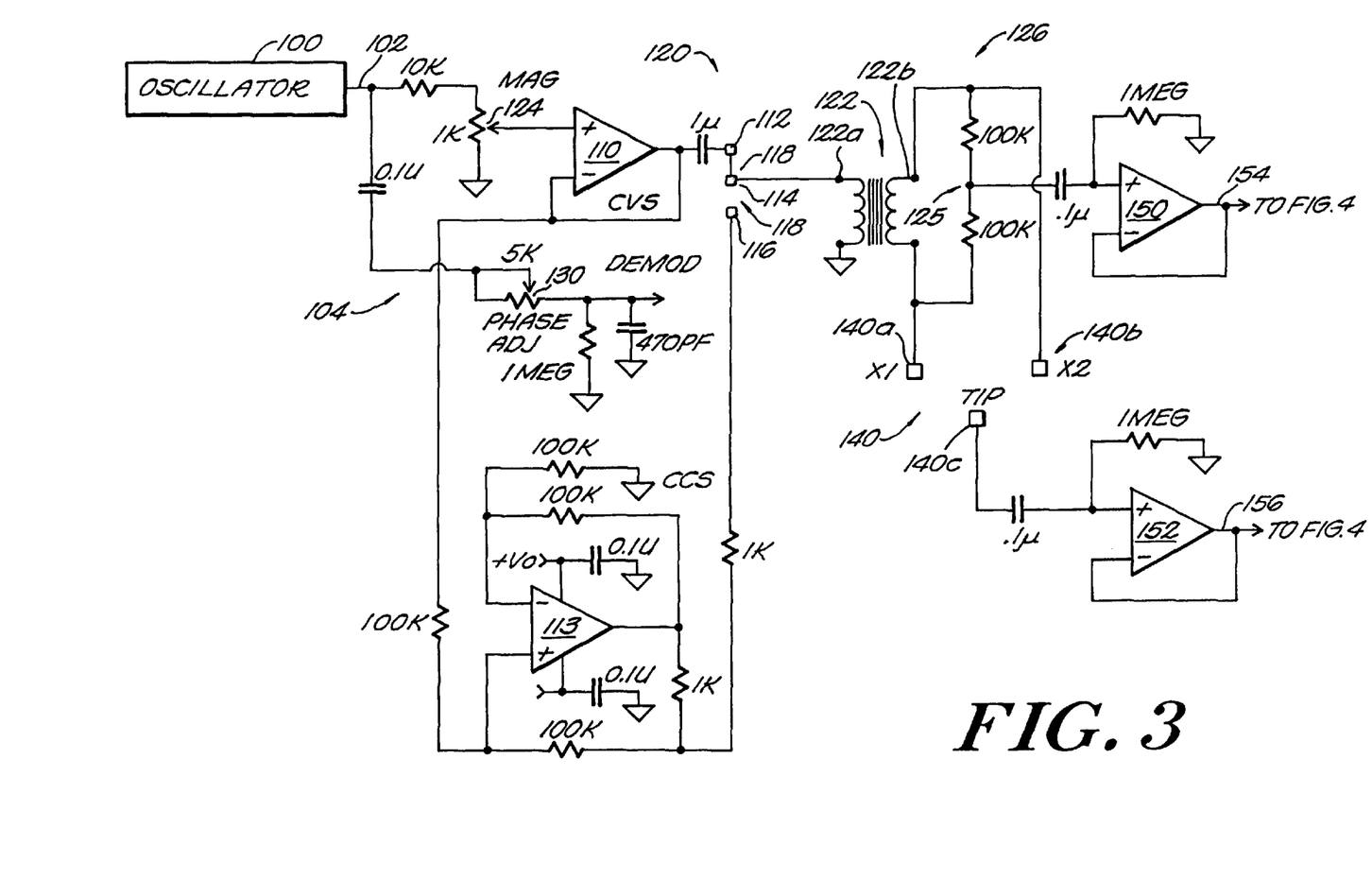
FIG. 3 is a schematic of the front end circuit of the catheter positioning system of FIG. 2.

Referring also to FIG. 3, the front end circuit 120 includes a gain and/or phase stage 104, an electrode interface 126 and buffers 150, 152. The output signal 102 from the X axis oscillator 100 is coupled to the gain and/or phase stage 104 which permits the magnitude of the AC energy signal 102 and/or the phase of demodulation of the signal from the X axis reference electrodes 40a, 40b to be adjusted. More particularly, the oscillator output signal 102 is coupled to a first potentiometer 124 which can be adjusted to vary the magnitude of the oscillator output signal 102. The oscillator output signal 102 is further coupled to a second potentiometer 130 which is adjustable to vary the phase of demodulation of the signal from the reference electrodes 40a, 40b. More particularly, the output of the potentiometer 130 provides a phase signal (DEMODX) which is coupled to the demodulator switch 132 (FIG. 5). The phase signal is used to vary the demodulation phase in order to compensate for phase shifts resulting from signal processing.

The magnitude setting potentiometer 124 is coupled to an operational amplifier 110 which provides a voltage output signal at a circuit node 112. The output of voltage amplifier 110 is further coupled to an operational amplifier 113 which provides a current output signal at a circuit node 116. A jumper 118 is provided for selectively connecting either the voltage output of amplifier 110 or the current output of amplifier 113 to a circuit node 114. With this arrangement, the jumper 118 can be positioned in order to provide an AC current or an AC voltage to the reference electrodes 40a, 40b. In the preferred embodiment, an AC current is supplied to the reference electrodes 40a, 40b, since this stimulus type provides a larger signal-to-noise ratio.

A transformer 122 coupled to the circuit node 114 isolates the oscillator 100 on the primary side 122a of the transformer from the reference electrodes 40a, 40b coupled to the secondary side 122b of the transformer. The X axis reference electrodes 40a, 40b are coupled to the signal processor 14 via respective terminals 140a, 140b of connector 140, as shown. More particularly, the terminals 140a, 140b are coupled to a buffer 150 via a resistor divider 125. The detection electrode 38 of the catheter 30 is coupled to the signal processor 14 via terminal 140c of connector 140. A buffer 152 buffers the electrical signal from the detection electrode 38. The output signals 154, 156 of buffers 150, 152, respectively, are coupled to the demodulator circuit 128 (FIG. 4).

Figure 4:
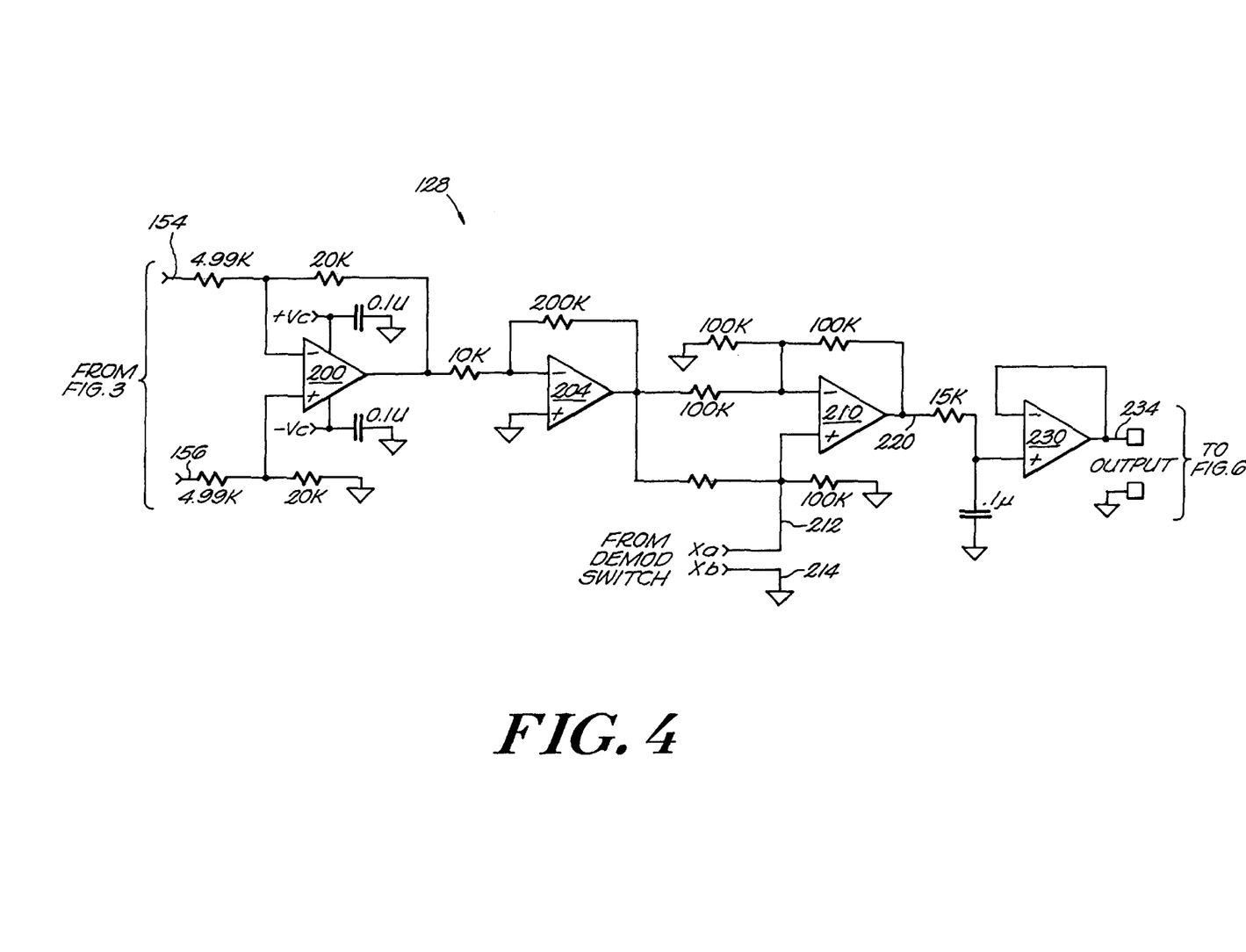
FIG. 4 is a schematic of the demodulator circuit of the catheter positioning system of FIG. 2.

Referring to FIG. 4, the demodulator circuit 128 includes a differential amplifier 200 having a first input coupled to the output 154 of buffer 150 (FIG. 3) and a second input coupled to the output 156 of buffer 152 (FIG. 3). The output of the differential amplifier 200 is coupled to a gain stage 204, as shown. Demodulation is provided by an amplifier 210 having an inverting input coupled to the output of the gain stage 204 and a non-inverting input coupled to the output of the gain stage 204 and further to a signal line 212 from the demodulator switch 132, as will be described below in conjunction with FIG. 5.

In operation, the differential voltage indicative of impedance between the reference electrodes 40a, 40b and the detection electrode 38 is measured by differential amplifier 200 such that the output of amplifier 200 is an AC signal having a polarity and magnitude indicative of the position of the detection electrode 38 relative to the reference electrodes 40a, 40b. That is, a positive output signal indicates that the detection electrode 38 is closer to one of the electrodes 40a, 40b and a negative output signal indicates that the detection electrode 38 is closer to the other one of the electrodes 40a, 40b. Thus, when the output signal of the amplifier 200 is null, the detection electrode 38 is equidistantly positioned between the X axis reference electrodes 40a, 40b. The magnitude of the output signal of the amplifier 200 indicates the relative proximity of the detection electrode 38 to each of the reference electrodes 40a, 40b.

The gain of the output signal of amplifier 200 is boosted by the gain stage 204 in order to enhance the detection sensitivity. For example, in the illustrative embodiment, the gain is boosted by a factor of twenty. The output of the gain stage 204 is demodulated by demodulator 210 in accordance with signals Xa and Xb provided by the demodulator switch 132 (FIG. 5) in response to the respective phase signal DEMODX, as will be described.

Referring also to FIG. 5, the demodulator switch 132 provides demodulation input signals Xa/Xb, Ya/Yb and Za/Zb to the processor units 50, 52, and 54, respectively, as shown in FIG. 2. The demodulator switch 132 is responsive to phase signals DEMODX, DEMODY and DEMODZ (FIG. 2) from the phase portion of circuitry 104 of the front-end circuit 120 of each the X, Y and Z processor units 50, 52 and 54. More particularly, each of the DEMOD signals is coupled to a respective comparator 250, 252 and 254, as shown and the output of each of the comparators 250, 252, and 254 is coupled to an analog switch 260.

Switch 260 includes three inverters, each having an input coupled to an output of a respective one of the comparators 250, 252, 254. For example, the output of the X axis comparator 250 is coupled to the input of inverter 264. Each inverter has a switch associated therewith that is adapted for being in a first, open position when the inverter output signal is in one logic state and in a second, closed position when the inverter output signal is in the second logic state. In the illustrative example, when the output signal of the inverter 264 is at a logic low level, the switch 262 is open, so that terminals 262a and 262b are disconnected, as shown. When the inverter output signal is at a logic high level, the corresponding switch 262 is closed, with terminals 262a and 262b electrically connected.

Referring again to FIG. 4, switch 262 is coupled between signal lines 212 and 214 such that, when the switch 262 is closed, signal line 212 is connected to ground via signal line 214. Whereas, when the switch 262 is open, signal line 212 is floating. With this arrangement, the signal provided at the output of amplifier 204 is demodulated with respect to the phase signal (DEMODX). The output signal 220 of the demodulator 210 is thus a DC signal with varying amplitude having a mean value proportional to the position of the catheter 30 relative to the X axis (i.e., proportional to the X coordinate). An amplifier 230 forms a low-pass filter for establishing the mean value, in order to enhance the detection accuracy of the system. The filter output signal 234, referred to alternatively as the demodulated catheter position signal 234, is coupled to the sampling circuit 134 (FIG. 6). The information from channels Y 52 and Z 54 present on channel X are also demodulated. However, since they are not synchronous with the demodulation signal, an AC signal is generated and this information is averaged to zero by the filter.

Referring to FIG. 6, the sampling circuit 134 controls the sampling of the demodulated catheter position signal 234 (FIG. 4) in order to generate the X axis output signal 62. More particularly, as noted above, the catheter positioning system 10 is adapted for operating in a "direct" mode of operation, during which the catheter position is continuously tracked, or in a "relative" mode of operation, in which the catheter position is recorded and subsequent catheter positions are detected relative to the recorded position.

To this end, a four-pole, double throw direct/relative switch 310 is provided for user control in order to select between the direct and relative modes of operation. Switch pole 310a is associated with the X axis processor unit 50 (FIG. 6), pole 310b is associated with the Y axis processor unit 52 (FIG. 2) and pole 310c is associated with the Z axis processor unit 54 (FIG. 2). The fourth pole 310d of the switch 310 is common to all three of the processor units and is provided for controlling the sample and hold circuit 304, as will be described.

The demodulated catheter position signal 234 is coupled to a differential amplifier 300, the input of sample and hold circuit 304 and switch 310a, as shown. The output of the sample and hold circuit 304 is coupled to an input of the differential amplifier 300, the output of which is coupled to the switch 310a. Switch 310a selectively couples the non-inverting input of a gain stage 320 either to the catheter position signal 234 or to the output of operational amplifier 300. When the switch 310 is in the direct position, as shown, the non-inverting input of the gain stage 320 is coupled to the demodulated catheter position signal 234. Alternatively, when the switch 310 is in the relative position, the non-inverting input of gain stage 320 is coupled to the output of the amplifier 300. The output signal of amplifier 300 represents the catheter's position relative to the catheter's position when the switch 310 was in the direct position.

Switch 310d causes the S/H input of the sample and hold circuit 304 to be selectively coupled to +5V or to ground, as shown. When the switch 310 is in the direct position and the S/H input to the sample and hold circuit 304 is at +5V, the sample and hold circuit 304 tracks the signal 234 to provide output signal 316. When the switch 310 is in the relative position and the S/H input to the sample and hold circuit 304 is at ground, the output signal 316 of the sample and hold circuit 304 is held constant.

The gain of the operational amplifier 320 is adjustable in order to adjust the position detection sensitivity. To this end, a switch 330 is provided in feedback relationship with the gain stage 320 to selectively connect or disconnect the output of gain stage 320 to its inverting input. In this way, the gain of amplifier 320 can be set to one or to a gain set by resistors 322 and 323.

The output signal 328 of the gain stage 320 is coupled to the input of a sample and hold circuit 324 which is operative to track and sample the signal 328 in accordance with the SYNC signal 107. This sampling stage serves to reduce artifacts associated with the patient's EKG and/or respiratory signals, as will be described. The output of the sample and hold circuit 324 is a DC signal 62 (FIG. 2) indicative of the X coordinate of the catheter position during the direct mode of operation or indicative of the difference between the X coordinate of the catheter position and a recorded catheter position during the relative mode of operation. Thus, the display 60 can display the catheter position relative to a previous position or the direct catheter position measurements relative to an arbitrary origin. For example, multiple catheter positions relative to the X, Y and Z axes may be captured and displayed.

In operation, when the switch 310 is in the direct position, the demodulated catheter position signal 234 is tracked by the sample and hold circuit 304 and is coupled to the gain stage 320 for processing and coupling to the input of the sample and hold circuit 324. The signal 328 is thus indicative of the present X coordinate of the catheter and is sampled by the circuit 324 every time the SYNC signal 107 transitions to a logic high level.

When the switch 310 is toggled to the relative position, the sample and hold circuit 304 causes the previously tracked catheter position signal 234 to be held to provide the output signal 316. Further, the output of the differential amplifier 300 is coupled to the gain stage 320 for processing and coupling to the sample and hold circuit 324. In this mode of operation, the signal 328 is indicative of the difference between the present X coordinate of the catheter (i.e., as represented by the catheter position signal 234) and its position at the time that the switch 310 was toggled (i.e., as represented by the value held at the output 316 of the sample and hold circuit 304). Stated differently, the differential amplifier 300 detects the difference between the signal 316 which is indicative of the catheter X coordinate when the switch 310 was toggled (i.e., the recorded position) and the X coordinate of the present catheter position (i.e., the subsequent position) and it is this difference signal that is coupled to the gain stage 320 and to the sample and hold circuit 324 to provide the X axis output signal 62 to the display 60.

Figure 7:
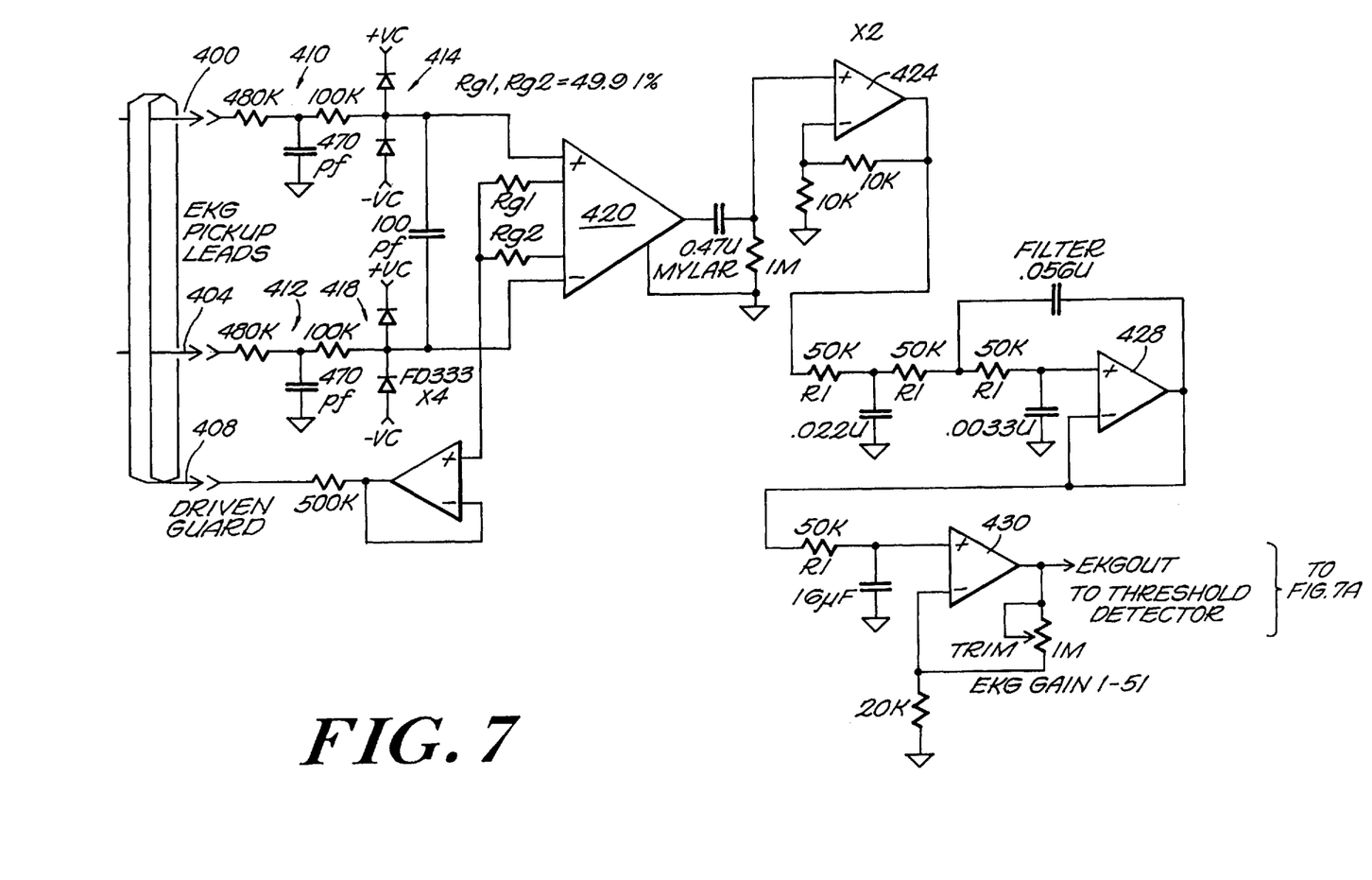
FIG. 7 is a schematic of a first portion of the EKG circuit of the catheter positioning system of FIG. 2.
Figure 7A:
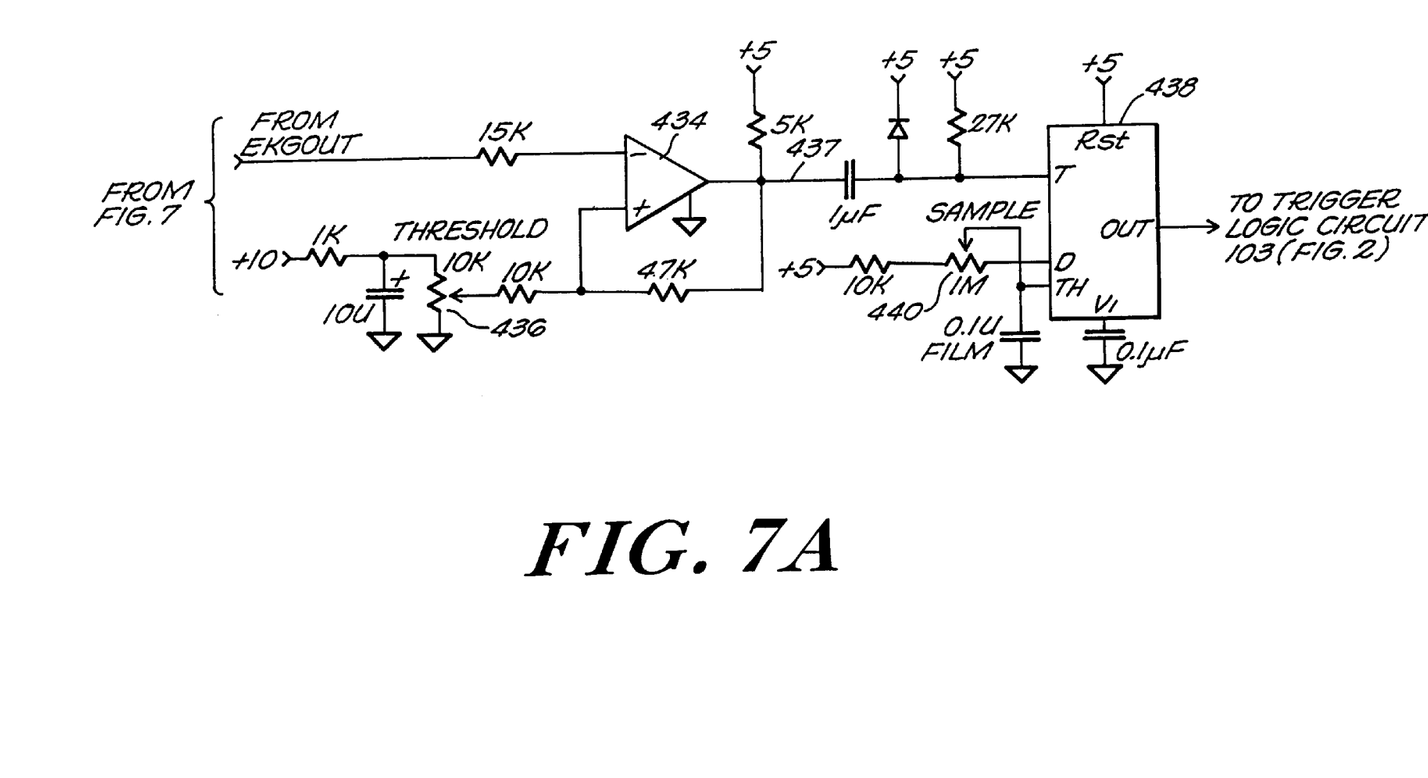
FIG. 7A is a schematic of a second portion of the EKG circuit of the catheter positioning system of FIG. 2.

Referring to FIGS. 7 and 7A, the EKG circuit 105 (FIG. 2) is shown to include three leads 400, 404 and 408 adapted for attachment to the patient. Two of the leads 400 and 404 are pickup leads and the third lead 408 is a guard, or reference lead. The leads 400 and 404 are coupled to respective filter circuits 410 and 412 and to optional protection devices 414 and 418, as shown. The filtered signals are further coupled to a differential amplifier 420.

The output of the differential amplifier 420 is coupled to an amplifier 424 for signal amplification and further to a low-pass filter 428. The output of filter 428 is coupled to an adjustable gain stage 430 to provide an output signal EKGOUT, as shown. In the illustrative embodiment, the gain can be adjusted from between one and fifty-one.

The EKGOUT signal is coupled to a first input of a threshold detection comparator 434 (FIG. 7A), the second input to which receives an adjustable threshold voltage. More particularly, the threshold voltage is adjustable with a potentiometer 436. The output signal 437 of the comparator 434 is a logic signal for triggering a one shot 438. Preferably, the threshold level coincides with the r-wave of the detected EKG signal. It will be appreciated by those of ordinary skill in the art that the EKG detection circuitry shown and described herein is illustrative only and that other conventional EKG triggering circuitry and techniques could alternatively be used.

The one-shot circuit 438 generates a sampling pulse at a duration set by an adjustable resistor 440. The output of the one-shot 438 provides an EKG signal which transitions to a logic high level when the detected EKG signal exceeds the predetermined threshold level (i.e., when an r-wave is detected). The EKG signal is coupled to a trigger logic circuit 103 (FIG. 2) or, in applications in which the SYNC signal 107 is based only on the EKG signal, the output of the EKG signal is coupled directly to a switch 444 (FIG. 2).

The optional respiratory detector 101 (FIG. 2) includes similar circuitry and uses similar techniques to those described above in conjunction with EKG signal detection in order to detect the patient's respiratory signal. The output signal from the respiratory detector 101 is coupled to the trigger logic circuit 103 which combines the EKG signal and the respiratory signal to provide the SYNC signal 107 which indicates a predetermined point in the patient's respiratory and EKG cycles. The SYNC output signal of the trigger logic circuit 103 is coupled to a switch 444 which can be toggled between a SYNC position as shown and a "free-run" position in which the catheter position detection is not synchronized and the SYNC signal 107 is maintained at a logic high level, so that the X axis output signal 62 continuously tracks the input signal 328.

Figure 8:
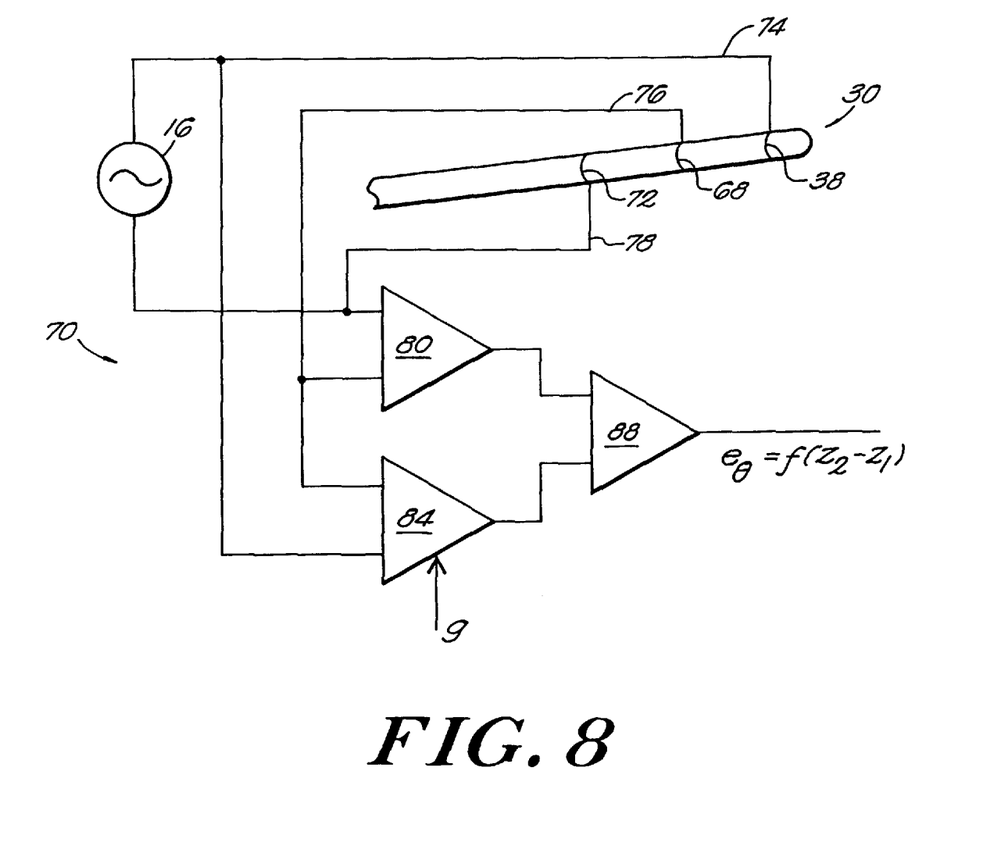
FIG. 8 is a schematic illustrating processing of signals from the detection, proximal and reference electrodes of the catheter of FIG. 1A in order to detect contact of the catheter with tissue.

Referring to FIG. 8, preferably, the signal processor 14 includes a catheter contact detection processor 70 for detecting contact of the catheter 30 with a vessel wall, or other tissue. Contact detection is achieved by providing a fourth current between the tip electrode 38 and the proximal electrode 72 and measuring the differential voltage representing impedance between the catheter electrodes, as described in U.S. Pat. No. 5,341,807 (Nardella) which is incorporated herein by reference.

More particularly, the energy source 16 is coupled between the tip electrode 38 and the proximal electrode 72 of the catheter to provide a current between the two electrodes. A first differential amplifier 80 has a first input coupled to the proximal electrode 72 and a second input coupled to the reference electrode 68. A second differential amplifier 84 has a first input coupled to the tip electrode 38 and a second input coupled to the reference electrode 68, as shown. With this arrangement, each of the differential amplifiers provides an output signal indicative of the impedance between the reference electrode 68 and a respective one of the proximal electrode 72 and tip electrode 38. The output of each of the differential amplifiers 80 and 84 is coupled to an input of a third differential amplifier 88 which detects a difference in the voltage representing a difference in the impedance between the tip electrode 38 and the reference electrode 68 and between the proximal electrode 72 and the reference electrode 68. When the impedance between electrodes 38 and 68 is substantially equal to the impedance between electrodes 68 and 72, the output of differential amplifier 88 is substantially null. Whereas, when the impedances differ (for example, as will occur when the tip electrode 38 contacts a vessel wall and the proximal electrode is disposed in blood), the output of the differential amplifier 88 increases. In this way, contact of the catheter 30 is indicated at the output of the differential amplifier 88 which may be coupled to a display (not shown).

Figure 9:
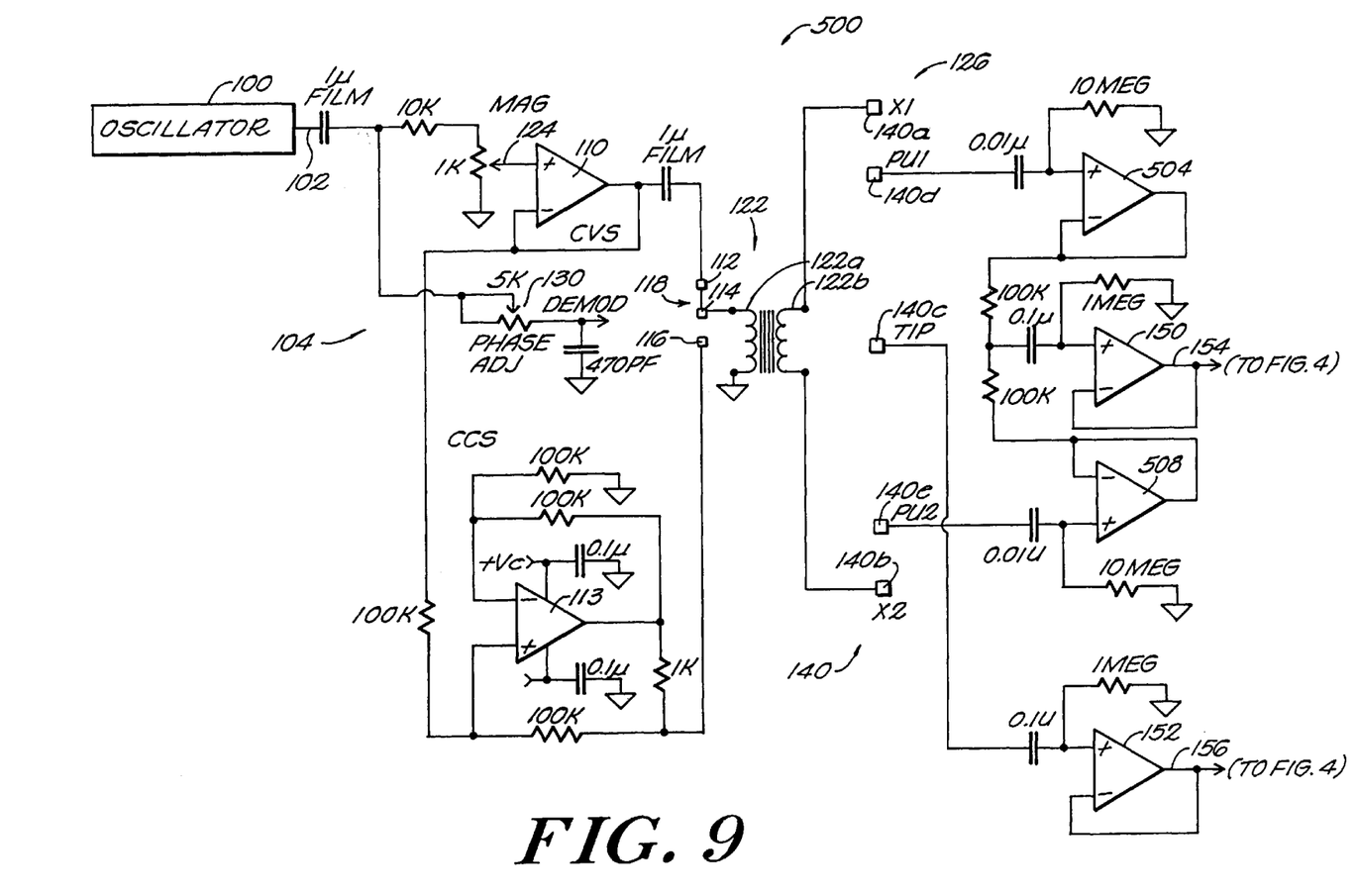
FIG. 9 is a schematic of an alternate front end circuit of the catheter positioning system of FIG. 2 including compensation electrodes for use in conjunction with externally attached reference electrodes.

Referring to FIG. 9, a schematic of an alternate front end circuit 500 of the catheter positioning system of FIG. 2 includes compensation electrodes for use in conjunction with externally attached reference electrodes 40a, 40b (FIG. 1). The front end circuit 500 is similar to the front end circuit 120 (FIG. 3), with like components being labelled with like reference numbers. Thus, the front end circuit 500 includes the gain and/or phase stage 104, the electrode interface 126 and buffers 150 and 152.

The front end circuit 500 differs from the front end circuit 120 of FIG. 3 in that the circuit 500 includes two additional electrodes, referred to as compensation electrodes PU1 and PU2, which are pad electrodes attached externally to the patient and electrically coupled to the signal processor via terminals 140d, 140e of connector 140. The compensation electrodes PU1 and PU2 are coupled to amplifiers 504 and 508, respectively, each of which has a high input impedance. Amplifier 504 has a non-inverting input capacitively coupled to the input terminal 140d and an inverting input coupled to its output. The output of amplifier 504 is further coupled to the resistor divider 125 (FIG. 3). Similarly, amplifier 508 has a non-inverting input capacitively coupled to the input terminal 140e and an inverting input coupled to its output. The output of amplifier 508 is further coupled to the resistor divider 125. Use of the compensation electrodes PU1 and PU2 serves to minimize any impedance variations associated with external attachment of the reference electrodes 40a, 40b to the patient.

It will be appreciated by those of ordinary skill in the art that the apparatus and techniques described herein may be used to detect the position of multiple detection electrodes which may be supported by a single catheter or, alternatively, may be supported by separate catheters. The signal processor of a multiple detection electrode system may comprise additional processor units (like processor units 50, 52, and 54 shown in FIG. 2) for each additional detection electrode. Alternatively, the signal processor units 50, 52 and 54 may be multiplexed to detect the position of the multiple detection electrodes. In addition to detection of the position of the multiple detection electrodes, this arrangement advantageously permits the direction of the electrodes to be determined. One application for such a system is atrial fibrillation, in which an elongated continuous lesion is created.

The foregoing description of the illustrative embodiments of the invention is presented to indicate the range of constructions to which the invention applies. Variations in the invention will be apparent to those having ordinary skill in the art based upon the disclosure herein, and such variations are considered to be within the scope of the invention in which patent rights are asserted, as set forth in the claims appended hereto. All publications and references cited herein are expressly incorporated herein by reference in their entirety.

What is claimed is:

1. An apparatus for detecting a position of a catheter in contact with a patient, said position characterized by an X coordinate relative to an X axis, a Y coordinate relative to a Y axis, and a Z coordinate relative to a Z axis, comprising:
    a catheter;
    a detection electrode disposed on the catheter;
    a first set of reference electrodes disposed along the X axis;
    a second set of reference electrodes disposed along the Y axis;
    a third set of reference electrodes disposed along the Z axis; and
    a signal processor for measuring the differential voltage indicative of impedance between the detection electrode and a first reference potential electronically generated between each electrode of the first set of reference electrodes in order to determine the X coordinate, the differential voltage indicative of impedance between the detection electrode and a second reference potential electronically generated between each electrode of the second set of reference electrodes in order to determine the Y coordinate and the differential voltage indicative of impedance between the detection electrode and a third reference potential electronically generated between each electrode of the third set of reference electrodes in order to determine the Z coordinate.

2. The apparatus of claim 1 wherein the catheter is an ablation catheter and the detection electrode is an active electrode which is adapted to be coupled to an energy source for delivering electrical energy to a treatment site of the patient.

3. The apparatus of claim 1 wherein the first, second and third sets of reference electrodes are needle electrodes adapted to be inserted into the patient.

4. The apparatus of claim 1 wherein the first, second and third sets of reference electrodes are pad electrodes adapted to be attached externally to the patient.

5. The apparatus of claim 4 further comprising a first set of compensation electrodes disposed along the X axis and associated with the first set of reference electrodes, a second set of compensation electrodes disposed along the Y axis and associated with the second set of reference electrodes and a third set of compensation electrodes disposed along the Z axis and associated with the third set of reference electrodes.

6. The apparatus of claim 1 further comprising a display for displaying the X coordinate, Y coordinate and Z coordinate.

7. The apparatus of claim 1 wherein the signal processor comprises an X axis processor unit, a Y axis processor unit and a Z axis processor unit, wherein each processor unit comprises a differential amplifier having a first input coupled to the detection electrode and a second input coupled to the respective set of reference electrodes.

8. The apparatus of claim 7 wherein each processor unit further comprises a demodulator coupled to the output of the differential amplifier for providing a DC signal proportional to the coordinate relative to the respective axis.

9. The apparatus of claim 1 wherein the detection electrode is disposed at a tip of the catheter and the catheter further comprises a plurality of ring electrodes and wherein the signal processor further measures the differential voltage indicative of impedance between the tip electrode and selected ones of the plurality of ring electrodes in order to determine whether the catheter is in contact with tissue.

10. The apparatus of claim 1 further comprising a sensor for detecting an EKG signal of the patient, wherein said signal processor operates in synchronization with the EKG signal.

11. The apparatus of claim 1 further comprising a sensor for detecting a respiratory signal of the patient, wherein the signal processor operates in synchronization with the respiratory signal.

12. The apparatus of claim 1 wherein a first current adapted to be provided by an energy source flows between the first set of reference electrodes, a second current adapted to be provided by the energy source flows between the second set of reference electrodes and a third current adapted to be provided by the energy source flows between the third set of reference electrodes, and wherein the first, second and third currents have different frequencies relative to one another.

13. The apparatus of claim 1 comprising multiple detection electrodes disposed on the catheter.

14. A method for detecting a position of a catheter in contact with a patient, said position characterized by an X coordinate relative to an X axis, a Y coordinate relative to a Y axis and a Z coordinate relative to a Z axis, comprising the steps of:
    positioning a detection electrode on the catheter;
    inserting into a patient a first set of reference electrodes, each disposed on a needle to position said electrodes along the X axis;
    inserting into a patient a second set of reference electrodes, each disposed on a needle to position said electrodes along the Y axis;
    inserting into a patient a third set of reference electrodes, each disposed on a needle to position said electrodes along the Z axis;
    measuring the differential voltage indicative of impedance between the detection electrode and each electrode of the first set of reference electrodes in order to determine the X coordinate;
    measuring the differential voltage indicative of impedance between the detection electrode and each electrode of the second set of reference electrodes in order to determine the Y coordinate; and
    measuring the differential voltage indicative of impedance between the detection electrode and each electrode of the third set of reference electrodes in order to determine the Z coordinate.

15. The method of claim 14 further comprising the step of treating the patient by delivering electrical energy to a treatment site of the patient from the detection electrode.

16. The method of claim 14 wherein each of the reference electrode positioning steps comprises attaching the respective set of reference electrodes externally to the patient.

17. The method of claim 14 further comprising the step of displaying the X coordinate, Y coordinate and Z coordinate.

18. The method of claim 14 further comprising the steps of:
    detecting an EKG signal of the patient; and
    performing the differential voltage measuring steps in synchronization with the EKG signal.

19. The method of claim 14 further comprising the steps of:
    detecting a respiratory signal of the patient; and
    performing the differential voltage measuring steps in synchronization with the respiratory signal.

20. The method of claim 14 further comprising the step of detecting contact of the catheter with tissue.

21. The method of claim 14 further comprising the step of positioning a plurality of detection electrodes on the catheter.

22. An apparatus for detecting a position of a catheter in contact with a patient, said position characterized by an X coordinate relative to an X axis, a Y coordinate relative to a Y axis, and a Z coordinate relative to a Z axis, comprising:
    a detection electrode disposed on the catheter;
    a first set of reference electrodes disposed along the X axis;
    a second set of reference electrodes disposed along the Y axis;
    a third set of reference electrodes disposed along the Z axis;
    a signal processor for measuring the differential voltage indicative of impedance between the detection electrode and each electrode of the first set of reference electrodes in order to determine the X coordinate, the differential voltage indicative of impedance between the detection electrode and each electrode of the second set of reference electrodes in order to determine the Y coordinate and the differential voltage indicative of impedance between the detection electrode and each electrode of the third set of reference electrodes in order to determine the Z coordinate; and
    a sensor for detecting an EKG signal of the patient, wherein said signal processor operates in synchronization with the EKG signal.

23. An apparatus for detecting a position of a catheter in contact with a patient, said position characterized by an X coordinate relative to an X axis, a Y coordinate relative to a Y axis, and a Z coordinate relative to a Z axis, comprising:
    a detection electrode disposed on the catheter;
    a first set of reference electrodes disposed along the X axis;
    a second set of reference electrodes disposed along the Y axis;
    a third set of reference electrodes disposed along the Z axis;
    a signal processor for measuring the differential voltage indicative of impedance between the detection electrode and each electrode of the first set of reference electrodes in order to determine the X coordinate, the differential voltage indicative of impedance between the detection electrode and each electrode of the second set of reference electrodes in order to determine the Y coordinate and the differential voltage indicative of impedance between the detection electrode and each electrode of the third set of reference electrodes in order to determine the Z coordinate; and
    a sensor for detecting a respiratory signal of the patient, wherein said signal processor operates in synchronization with the respiratory signal.

* * * * *